United States Patent [19]

Canada

[11] 4,380,641

[45] Apr. 19, 1983

[54] INSECTICIDAL OXAZOLYL UREAS

[75] Inventor: Emily J. Canada, Indianapolis, Ind.

[73] Assignee: Eli Lilly and Company, Indianapolis, Ind.

[21] Appl. No.: 315,130

[22] Filed: Oct. 26, 1981

[51] Int. Cl.$^3$ .................... C07D 263/34; A01N 43/28
[52] U.S. Cl. .................................... 548/233; 424/272; 564/60
[58] Field of Search ........................................ 548/233

[56] References Cited

U.S. PATENT DOCUMENTS

| | | | |
|---|---|---|---|
| 3,547,940 | 12/1970 | Brantley | 260/307 |
| 4,014,876 | 3/1977 | Sumimoto et al. | 360/247 |
| 4,062,861 | 12/1977 | Yukinaga et a. | 260/307 |
| 4,163,784 | 8/1979 | Holland | 424/246 |
| 4,336,264 | 6/1982 | Wickiser | 424/272 |

FOREIGN PATENT DOCUMENTS

| | | |
|---|---|---|
| 2881 | 11/1979 | European Pat. Off. |
| 53-86033 | 7/1978 | Japan. |
| 54-59272 | 5/1979 | Japan. |
| 1580876 | 12/1980 | United Kingdom. |

OTHER PUBLICATIONS

Oliver et al., Jour. Agr. Food Chemistry, 24, No. 5, pp. 1065–1068 (1976), "Insect Growth Regulators, Analogues of TH–6038 & TH–6040".

Wellinga et al., Jour. Agr. Food Chem., 21, No. 3, pp. 348–354, (1973) "Synthesis & Lab. Eval. of 1-(2-,6-disubstituted benzoyl)-3-phenyl ureas, a New Class of Insecticides I. 1-(2,6-dichlorobenzyl)-3--phenyureas".

DeMilo et al., J. Agric., Food Chem., 216, No. 1, pp. 164–166 (1978) "Heterocyclic Analogues Defluhenzuron as Growth & Reproduction Inhibitors of Fall Armyworm & House Flys".

C & E News pp. 24 & 57 Jul. 25, 1977 Issue. Final Program for 1977 ACS Meeting. Talk No. 73 by DeMilo et al.

Abstracts of Papers from 174th ACS Meeting 1977 Abstract of Talk No. 73 by DeMilo et al.

DeMilo et al. "Heterocyclic . . . Fly." J. Agr. Food Chem. 26, 164 (1978). Presented orally at 174th ACS Meeting, 1977.

*Primary Examiner*—Donald G. Daus
*Assistant Examiner*—Sharon A. Gibson
*Attorney, Agent, or Firm*—Kathleen R. S. Page; Arthur R. Whale

[57] ABSTRACT

1-(2,6-disubstituted benzoyl)-3-(4-alkoxycarbonyl-5-oxazolyl)ureas useful as insecticides.

10 Claims, No Drawings

INSECTICIDAL OXAZOLYL UREAS

SUMMARY OF THE INVENTION

The present invention relates to a compound of the formula

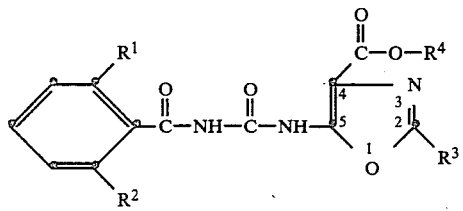

wherein:
- $R^1$ is halogen or methoxy;
- $R^2$ is hydrogen or halogen;
- $R^3$ is hydrogen, methyl or ethyl;
- $R^4$ is $C_1$–$C_4$ alkyl;

with the provisos that when $R^4$ is ethyl and one of $R^1$ and $R^2$ is chlorine, the other of $R^1$ and $R^2$ must be other than chlorine; and when $R^2$ is hydrogen and $R^4$ is ethyl, $R^1$ is other than chlorine.

The present invention also provides an insecticidal method for the use of such novel compounds, as well as compositions containing such compounds.

DETAILED DESCRIPTION OF THE INVENTION

The benzoyl oxazolyl ureas of the present invention are prepared by methods currently known in the art. The preferred synthetic method for the preparation of these compounds involves reacting an alkyl cyanoacetate with an appropriate alkanoic acid and alkanoic anhydride in the presence of sodium hydrosulfite and sodium nitrite to give the corresponding amide. The amide is cyclized in acid to give a 2-substituted-4-alkoxycarbonyl-5-aminooxazole, which is finally reacted with an appropriate 2,6-disubstituted benzoylisocyanate to give the corresponding 1-(2,6-disubstituted-benzoyl)-3-(2-substituted-4-alkoxycarbonyl oxazolyl)urea.

The 2,6-disubstituted benzoylisocyanate starting materials used to prepare compounds of the present invention are also prepared by procedures as well known in the art. The preferred route involves reacting a 2,6-disubstituted benzoyl chloride with anhydrous ammonia to give the corresponding benzamide, which is then reacted with oxalyl chloride to give a 2,6-disubstituted benzoylisocyanate.

The complete reaction scheme for the above-described procedure is as follows:

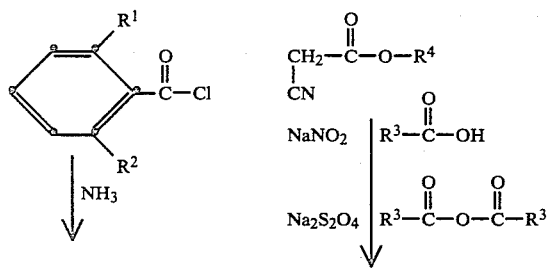

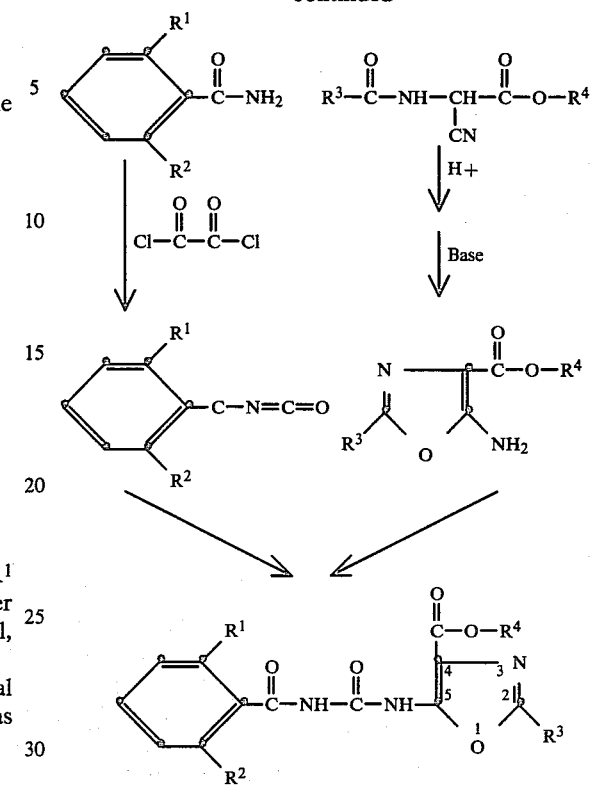

The final step of the above-described reaction is generally performed in a suitable solvent and in an inert atmosphere. Suitable solvents should be water-free and include most polar-aprotic solvents, with acetonitrile being preferred. The temperature range of the reaction mixture can be from 0° C. to 30° C. with 10° C. to 25° C. being preferred. Usually following addition of the reactants the mixture is stirred from about one to about 24 hours, and then worked up according to standard procedures. Typically, either the precipitated solid is collected or the solvent is removed in vacuo. The product may then be further purified by either recrystallization or column chromatography according to standard procedures.

The substituted acid chloride and cyanoacetate starting materials are either commercially available or readily prepared by known methods.

A typical preparation of the starting materials used to prepare compounds of the present invention is represented by the following:

N-(carbethoxycyanomethyl)propionamide

To 16 g. sodium nitrite, 60 ml. water and 22.6 g. ethyl cyanoacetate cooled to approximately 5° C. was added 16 ml. propionic acid. After stirring the reaction mixture at 0°–5° C. for 1.5 hours, 200 g. ice and 50 ml. propionic anhydride were added. Finally, 70 g. sodium hydrosulfite was added in portions over a time period of from about 5 to about 10 minutes. Stirring was continued for one hour, and the precipitated solid was collected by filtration. The solids were then washed with 60 ml. hot acetone and recrystallized from ether-petroleum ether. The structure was verified by NMR. Yield 6.8 g.

2-ethyl-4-carbethoxy-5-aminooxazole hydrochloride

Through a solution of 9.8 g. N-(carbethoxycyanomethyl)propionamide dissolved in 100 ml. anhydrous acetone was bubbled anhydrous HCl for about 2 hours while maintaining the temperature between about 20° and 30° C. Ether was added to aid the formation of a precipitate, which was then collected to yield 9.9 g.

2-ethyl-4-carbethoxy-5-aminooxazole

To 9.9 g. 2-ethyl-4-carbethoxy-5-aminooxazole hydrochloride was added 90 ml. dichloromethane and 30 ml. saturated sodium bicarbonate solution. Sodium carbonate was then added to the solution until the pH was approximately 9. The aqueous layer was extracted with $CH_2Cl_2$, dried over anhydrous magnesium sulfate, and concentrated. The solid was recrystallized from ethanol to yield 5.8 g. The structure was verified by NMR.

M.P.=115°–119° C.

Analysis calculated for $C_8H_{12}N_2O_3$

Theory: C, 52.17; H, 6.57; N, 15.21; Found: C, 52.37; H, 6.32; N, 15.02.

Starting with the appropriate 2,6-disubstituted benzoylisocyanate and substituted aminooxazole, compounds of the present invention can be prepared. Typical of these compounds are the following examples.

EXAMPLE 1

1-(2,6-difluorobenzoyl)-3-(2-ethyl-4-carbethoxy-5-oxazolyl)urea

To 0.5 g. 2-ethyl-4-carbethoxy-5-aminooxazole dissolved in 20 ml. acetonitrile was added 0.7 g. 2,6-difluorobenzoylisocyanate under nitrogen at about 25° C. The reaction mixture was stirred at about 25° C. for 3 hours and the solid was collected. Yield 0.36 g.

M.P.=171°–177° C.

Analysis calculated for $C_{16}H_{15}F_2N_3O_5$

Theory: C, 52.32; H, 4.09; N, 11.44; Found: C, 52.61; H, 3.85; N, 11.36.

EXAMPLE 2

1-(2-chloro-6-fluorobenzoyl)-3-(2-methyl-4-carbethoxy-5-oxazolyl)urea

To 0.6 g. 2-methyl-4-carbethoxy-5-aminooxazole dissolved in 25 ml. acetonitrile was added 0.8 2-chloro-6-fluorobenzoylisocyanate under nitrogen at about 25° C. The reaction mixture was stirred at 25° C. for 12 hours and the solid was collected. Yield 0.7 g.

M.P.=196°–202° C.

Analysis calculated for $C_{15}H_{13}ClFN_3O_5$

Theory: C, 48.73; H, 3.54; N, 11.37; Found: C, 48.74; H, 3.36; N, 11.40.

EXAMPLE 3

1-(2,6-difluorobenzoyl)-3-(2-methyl-4-carbethoxy-5-oxazolyl)urea

To 0.6 g. 2-methyl-4-carbethoxy-5-aminooxazole dissolved in 25 ml. acetonitrile was added 0.8 g. 2,6-trifluorobenzoylisocyanate under nitrogen at about 25° C. The reaction mixture was stirred at 25° for 12 hours and the solid was collected. Yield 0.97 g.

M.P.=199°–204° C.

Analysis calculated for $C_{15}H_{13}F_2N_3O_5$

Theory: C, 51.00; H, 3.71; N, 11.89; Found: C, 51.20; H, 3.82; N, 11.83.

The following compounds of the present invention were prepared in similar fashion to the preceding synthetic procedures:

EXAMPLE 4

1-(2-bromobenzoyl)-3-(2-methyl-4-carbethoxy-5-oxazolyl)urea

M.P.=180°–185° C.

Analysis calculated for $C_{15}H_{14}BrN_3O_5$

Theory: C, 45.47; H, 3.56; N, 10.61; Found: C, 45.18; H, 3.53; N, 10.40.

EXAMPLE 5

1-(2-methoxy-6-chlorobenzoyl)-3-(2-methyl-4-carbethoxy-5-oxazolyl)urea

M.P.=196°–199° C.

Analysis calculated for $C_{16}H_{16}ClN_3O_6$

Theory: C, 50.33; H, 4.19; N, 11.01; Found: C, 50.27; H, 4.08; N, 10.99.

EXAMPLE 6

1-(2-chloro-6-fluorobenzoyl)-3-(2-ethyl-4-carbethoxy-5-oxazolyl)urea

M.P.=174°–180° C.

Analysis calculated for $C_{16}H_{15}ClFN_3O_5$

Theory: C, 50.08; H, 3.94; N, 10.95; Found: C, 50.25; H, 4.12; N, 11.00.

The compounds of the present invention are useful for the control of insects of the order Lepidoptera. Members of this insect order include southern armyworm, codling moth, cutworm, clothes moth, Indian meal moth, leaf rollers, corn earworm, European corn borer, cabbage worm, cabbage looper, bollworm, bagworm, eastern tent caterpillar, sod webworm and fall armyworm.

It is believed that the compounds of the present invention function most effectively when the treated plant leaves are ingested by the insect for which control or eradication is desired. Generally, however, the compounds may be applied to or incorporated into any food or water source with which the insect comes into contact.

Therefore, the present invention also provides a method of suppressing insects of the order Lepidoptera which comprises applying to the locus of the insects an insecticidally-effective amount of a compound of the present invention. The locus can be any environment inhabited by the insects to be controlled, such as soil, air, water, food, vegetation, manure, inert objects, grain and the like.

The term "insecticidally-effective amount" refers to an amount which results in the inactivation of the insect. Such inactivation can kill the insect or render the insect incapable of performing one or more of its normal life processes. This amount will generally be from about 2000 ppm to 1 ppm, with the preferred insecticidal application rates ranging from about 1000 ppm to 10 ppm. It is, of course, apparent that higher or lower concentrations can be employed depending on the insect species to be controlled, the locus to which the application is to be made, the potency or toxicity of the particular compound, and the like.

It is believed that the present compounds interfere with the mechanism of metamorphosis which occurs in the insects thereby incapacitating them. However, the precise mechanism by which the present novel compounds function is not yet known, and the insecticidal method of the present invention is not limited by any mode of operation.

The compounds of the present invention are preferably formulated with an agriculturally-acceptable carrier for ease of application. Thus, for example, the present compounds can be in the form of a liquid, dust or granular composition depending on the locus for which insecticidal control is desired, costs and availability of materials, application techniques, and the like.

Liquid compositions containing the desired amount of active agent are prepared by dissolving the substance in an organic liquid or by dispersing the substance in water with or without the aid of a suitable surface-active dispersing agent such as an ionic or nonionic emulsifying agent. Such compositions also can contain modifying substances which serve to aid spreading and adhesion of the material on plant foliage. Suitable organic liquid carriers include the agricultural spray oils and the petroleum distillates such as diesel fuel, kerosene, fuel oil, naphthas, and Stoddard solvent. Among such liquids the petroleum distillates are generally preferred. The aqueous compositions can contain one or more water-immiscible solvents for the toxicant compounds. In such aqueous compositions, the carrier comprises an aqueous emulsion, e.g., mixture of water, emulsifying agents, and water-immiscible solvents. The choice of dispersing and emulsifying agent and the amount thereof employed is dictated by the nature of the composition and by the ability of the agent to facilitate the dispersing of the active agent in the carrier to produce the desired composition. Dispersing and emulsifying agents which can be employed in the compositions include the condensation products of alkylene oxides with phenols and organic acids, alkaryl sulfonates, polyoxyalkylene derivatives of sorbitan esters, complex ether alcohols, and the like. For a review of known surface active agents which are suitably employed in implementing the present invention, attention is directed to U.S. Pat. No. 3,095,299, second column, lines 25–36, and references cited therein.

In the preparation of dust compositions, the active ingredient is intimately dispersed in and on a finely-divided solid such as clay, talc, chalk, gypsum, limestone, vermiculite fines, perlite, and the like. In one method of achieving such dispersion, the finely-divided carrier is mechanically mixed or ground with the active agent.

Similarly, dust compositions containing a present compound can be prepared with various solid carriers such a bentonite, fuller's earth, attapulgite, and other clays having surface-active adsorptive properties. Depending upon the proportions of ingredients, these dust compositions can be employed as concentrates and subsequently diluted with additional adsortive-type solid carriers or with chalk, talc, or gypsum, or the like to obtain the desired amount of active ingredient in a composition adapted to be employed in accordance with the present invention. Also, such dust compositions can be dispersed in water, with or without the aid of a dispersing agent, or form spray mixtures.

Also the compositions of the present invention can be employed in granular formulations. These formulations are prepared in conventional manner, typically by dissolving the compound in a solvent with or without a surface-active agent and spraying or otherwise distributing the resulting solution onto pre-formed granules. Such granular formulations are capable of providing longer-lasting activity and may be preferred for crops such as corn where repeated application is not practical.

A compound of the present invention, or a composition thereof, may be applied to the locus for which insecticidal control is desired by any of the conventional methods familiar to those skilled in the art. Common application techniques include hand dusting or spraying, or by simply mixing the active agent with the food to be ingested by the insects. Application to the foliage of plants is typically performed with power dusters, boom sprayers, and fog sprayers. In large scale operations, dust or low volume sprays can be applied from the air.

The insecticidal activity of the present compounds was determined by testing the efficacy of formulations of the compounds against southern armyworm larvae (*Spodoptera eridania*). The test procedure is described in detail below.

EXPERIMENT 1

Test formulations were prepared by dissolving 11 milligrams of test compound in one milliliter of a solvent-emulsifier system. The solvent emulsifier system was prepared by adding 5.9 grams of Toximul R and 4.0 grams of Toximul S to a mixture of 500 milliliters of acetone and 500 milliliters of ethyl alcohol. (Toximul R and Toximul S are each a sulfonate nonionic emulsifier blend produced by Stepan Chemical Company, Northfield, Illinois). The solution was then diluted with 10 milliliters of water to provide a solution containing 1000 parts per million (ppm) test compound. One milliliter of this solution was diluted with nine milliliters of water to provide a formulation having a concentration of 100 parts per million test compound. The 10 ppm and 1 ppm concentrations were prepared by similar serial dilutions.

The test formulations were sprayed separately on the leaves of 4 to 6 day old bean plants. Adequate formulation to wet both tops and bottoms of the leaves was used. Spraying was performed with a DeVilbiss atomizer constructed by the DeVillbiss Company, Toledo, Ohio. During the spraying procedure the nozzle of the atomizer was held 12 to 18 inches from the leaves and was supplied at a pressure of 5–6 pounds per square inch. The leaves were allowed to dry completely, removed from the plants, and the cut ends wrapped in water-soaked cellucotton. Two treated leaves and five second and third instar southern armyworm larvae were placed in each of three 100×20 mm plastic petri dishes. Controls using untreated leaves were similarly prepared.

Certain of the compound formulations were recorded after two days. All of the dead larvae were counted at the end of four days. From the leaves remaining on the treated and untreated plants, enough leaves to add two additional leaves to each petri dish were removed. Two of these leaves were added to each petri dish following the four day evaluation, treated or untreated as appropriate. After three additional days, the final seven day mortality count was made.

Insecticidal effect was determined by counting the number of dead larvae of each species, and applying the following rating code.

| Dead Larvae | % Dead | Rating |
| --- | --- | --- |
| 0 | 0 | 0 |
| 1–2 | 1–50 | 1 |
| 3–4 | 51–99 | 2 |

| | -continued | |
|---|---|---|
| Dead Larvae | % Dead | Rating |
| 5 | 100 | 3 |

The results of this test are set forth in Table I.

TABLE I

| Compound of Example No. | Concentration (ppm) | Insect Control Day 2 | Day 4 | Day 7 |
|---|---|---|---|---|
| 1 | 100 | 0 | 2 | 3 |
|   | 10 | 0 | 0 | 0 |
|   | 1 | 0 | 0 | 0 |
| 2 | 1000 | 3 | 3 | |
|   | 100 | 1 | 2 | |
|   | 10 | 1 | 2 | |
|   | 1 | 1 | 2 | |
| 3 | 1000 | 2 | 2+ | |
|   | 100 | 1 | 2 | |
|   | 10 | 1 | 2 | |
|   | 1 | 1 | 2 | |
| 4 | 1000 | 0 | 0 | 1 |
|   | 100 | 0 | 0 | 0 |
|   | 10 | 0 | 0 | 0 |
|   | 1 | 0 | 0 | 0 |
| 5 | 1000 | 1 | 2 | 3 |
|   | 100 | 0 | 0 | 0 |
|   | 10 | 0 | 0 | 0 |
|   | 1 | 0 | 0 | 0 |
| 6 | 100 | 3 | 3 | 3 |
|   | 10 | 1 | 3 | 3 |
|   | 1 | 0 | 1 | 1 |

I claim:

1. A compound of the formula:

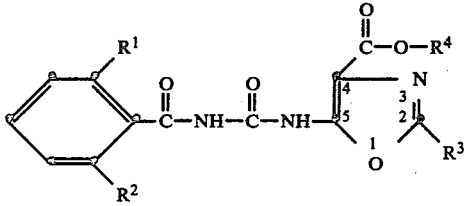

wherein:
$R^1$ is halogen or methoxy;
$R^2$ is hydrogen or halogen;
$R^3$ is hydrogen, methyl or ethyl;
$R^4$ is $C_1$–$C_4$ alkyl;
with the provisos that when $R^4$ is ethyl and one of $R^1$ and $R^2$ is chlorine, the other of $R^1$ and $R^2$ must be other than chlorine; and when $R^2$ is hydrogen and $R^4$ is ethyl, $R^1$ is other than chlorine.

2. A compound of claim 1 wherein $R^4$ is ethyl.

3. A compound of claim 2 wherein $R^3$ is methyl.

4. The compound of claim 3 which is 1-(2-chloro-6-fluorobenzoyl)-3-(2-methyl-4-carbethoxy-5-oxazolyl)urea.

5. The compound of claim 3 which is 1-(2,6-difluorobenzoyl)-3-(2-methyl-4-carbethoxy-5-oxazolyl)urea.

6. The compound of claim 3 which is 1-(2-bromobenzoyl)-3-(2-methyl-4-carbethoxy-5-oxazolyl)urea.

7. The compound of claim 3 which is 1-(2-methoxy-6-chlorobenzoyl)-3-(2-methyl-4-carbethoxy-5-oxazolyl)urea.

8. A compound of claim 2 wherein $R^3$ is ethyl.

9. The compound of claim 8 which is 1-(2,6-difluorobenzoyl)-3-(2-ethyl-4-carbethoxy-5-oxazolyl)urea.

10. The compound of claim 8 which is 1-(2-chloro-6-fluorobenzoyl)-3-(2-ethyl-4-carbethoxy-5-oxazolyl)urea.

* * * * *